(12) United States Patent
Carlucci et al.

(10) Patent No.: US 6,659,674 B2
(45) Date of Patent: Dec. 9, 2003

(54) ORAL IRRIGATOR AND BRUSH ASSEMBLY

(75) Inventors: Vito J. Carlucci, Stratford, CT (US); Paul Joseph Denhup, Stratford, CT (US); Dale S. Ziolkowski, Trumbull, CT (US)

(73) Assignee: Conair Corporation, Stamford, CT (US)

( * ) Notice: Subject to any disclaimer, the term of this patent is extended or adjusted under 35 U.S.C. 154(b) by 0 days.

(21) Appl. No.: 09/952,418

(22) Filed: Sep. 14, 2001

(65) Prior Publication Data

US 2003/0053847 A1 Mar. 20, 2003

(51) Int. Cl.[7] ............................................. A46B 11/06
(52) U.S. Cl. ..................... 401/289; 401/282; 433/82; 433/87
(58) Field of Search ................. 401/289, 290, 401/282, 291, 268; 433/80, 82, 87, 88, 89, 141

(56) References Cited

U.S. PATENT DOCUMENTS

| | | | | |
|---|---|---|---|---|
| 352,009 A | * | 11/1886 | Seery | 401/289 |
| 1,484,026 A | * | 2/1924 | Jacobs | 401/291 |
| 4,052,002 A | | 10/1977 | Stouffer et al. | 239/4 |
| 4,386,911 A | | 6/1983 | Maloney et al. | 433/125 |
| 4,580,588 A | * | 4/1986 | Swope, Jr. | 401/290 |
| 4,596,364 A | | 6/1986 | Bauer | 239/590 |
| 4,787,845 A | | 11/1988 | Valentine | 433/88 |
| 4,858,336 A | | 8/1989 | Varma | 34/90 |
| 4,863,302 A | * | 9/1989 | Herzfeld | 401/289 |
| 4,979,504 A | | 12/1990 | Mills | 128/66 |
| 5,086,756 A | | 2/1992 | Powell | 128/66 |
| 5,273,428 A | * | 12/1993 | Fischer | 433/80 |
| 5,351,417 A | | 10/1994 | Rubin | 34/90 |
| 5,365,624 A | | 11/1994 | Berns | 15/22.1 |
| 5,465,444 A | | 11/1995 | Bigler et al. | 15/22.1 |
| 5,568,691 A | | 10/1996 | Rubin | 34/98 |
| 5,577,285 A | | 11/1996 | Drossler | 15/22.1 |
| 5,593,225 A | | 1/1997 | Safyan | 362/427 |
| 5,651,211 A | | 7/1997 | Regan et al. | 43/113 |
| 5,755,572 A | | 5/1998 | Bab et al. | 433/80 |
| 5,771,471 A | | 6/1998 | Alberth, Jr. et al. | 455/573 |
| 5,800,367 A | | 9/1998 | Saxer et al. | 601/164 |
| 5,974,615 A | | 11/1999 | Schwarz-Hartmann et al. | 15/22.4 |
| 6,021,538 A | | 2/2000 | Kressner et al. | 15/28 |
| 6,030,215 A | | 2/2000 | Ellion et al. | 433/89 |
| 6,110,292 A | | 8/2000 | Jewett et al. | 134/1 |
| 6,152,733 A | | 11/2000 | Hegemann et al. | 433/80 |
| 6,176,941 B1 | | 1/2001 | Jewett et al. | 134/29 |
| 6,186,782 B1 | * | 2/2001 | Luppi | 433/82 |

\* cited by examiner

*Primary Examiner*—David J. Walczak
(74) *Attorney, Agent, or Firm*—Ohlandt, Greeley, Ruggiero & Perle, LLP

(57) ABSTRACT

An oral irrigator including a main body and a brush assembly. The main body has an elongated shaft, a connector connected to the elongated shaft, and a receiving cavity connected to the neck for receiving and retaining a brush assembly. The oral irrigator is adapted to work in conjunction with a mechanism for providing pressurized liquid (e.g. a pump).

14 Claims, 4 Drawing Sheets

ORAL IRRIGATOR AND BRUSH ASSEMBLY

BACKGROUND OF THE INVENTION

1. Field of the Invention

The present invention relates to an oral irrigator. More particularly, the present invention relates to an oral irrigator having an irrigating brush assembly for brushing and irrigating between teeth and in the gum line.

2. Description of the Prior Art

The cleaning of teeth and gums is a good way to promote health and personal hygiene. However, it can be difficult at times, to effectively reach and remove the plaque and debris caught between teeth and in the gum line. Thus, devices, such as the toothbrush and dental floss, have been developed for the purpose of more effectively cleaning these hard to reach areas. The effectiveness of the toothbrush and dental floss, notwithstanding their popularity, is often not enough to satisfactorily clean the plaque and debris that is fixed between the teeth and in the gum line. Thus, there is a need for an oral irrigation device or oral irrigator capable of dislodging and flushing out this hard to reach plaque and debris caught between the teeth and in the gum line.

Examples of different oral irrigators demonstrating the state of the art can be found in U.S. Pat. No. 5,800,367, U.S. Pat. No. 5,086,756 and U.S. Pat. No. 3,675,645. A common disadvantage, associated with existing oral irrigators, is that the dispensed stream of liquid often lacks sufficient fluid pressure to properly remove debris and especially plaque from between the teeth and in the gum line. Moreover, the fluid pressure necessary to remove effectively the plaque and debris may cause injury to the gums. Thus, devices have been developed that combine the process of brushing with that of irrigation in an effort to overcome the shortcomings of the oral irrigator. This combined brushing and irrigating action allows for the proper and safe removal of unwanted plaque and debris fixed between the teeth and in the gum line.

An example of an oral irrigator that combines irrigation with brushing is found in U.S. Pat. No. 4,386,911. This patent describes an irrigator adapted with a scrubbing structure that includes a scrubbing cup with a concave or depressed area having resilient scrubbing ribs and a channel through which irrigating fluid can be provided. In addition, the patent provides for a scrubbing cup, similar to that just described, but having a plurality of protuberances, which function to aid in the removal of plaque and debris. The drawback of this device is that the scrubbing cup is not well adapted to reach effectively the plaque and debris between the teeth and in the gum line.

Another example of an oral irrigator that combines brushing and irrigation is found in U.S. Pat. No. 6,030,215. This patent describes an irrigator having a first attachment comprising a toothbrush head that has rows (i.e. at least three) of longitudinally spaced bristles as well as a multitude of exit ports (i.e. at least four) connected to a conduit for passing fluid from a fluid source to the toothbrush head. The drawback of this configuration is that the dispensed streams of fluid exiting the multitude of ports may be sufficiently dissipated so as to do little to actually aid in the removal of plaque and debris.

Also, the described arrangement of the toothbrush head may not necessarily be the most effective arrangement for cleaning between teeth and in the gum line. In fact, the patent describes a second attachment specifically adapted for removal of plaque from between teeth. This second attachment has a brush portion with bristles that vary in length to form a cone-like structure, which enables the brush to be inserted between teeth. Thus, a second drawback associated with this device is that it is necessarily inefficient to have to remove a first attachment and replace it with a second attachment in order to perform different cleaning functions.

Moreover, none of the above-identified devices provide for an oral irrigator specifically adapted to conveniently and effectively brush and irrigate between teeth and in the gum line using a brush assembly having a plurality of brushing members radially disposed in a plurality of circular rows extending from a surface of one side thereof and a single fluid exit port centrally located therein.

SUMMARY OF THE INVENTION

It is an object of the present invention to provide an oral irrigator that enhances the irrigating action on the teeth and gums.

It is another object of the present invention to provide such an oral irrigator adapted to massage and stimulate the gums.

It is another object of the present invention to provide such an oral irrigator having a brush assembly configured to improve the scrubbing action on and between the teeth and in the gum line.

It is still another object of the present invention to provide such an oral irrigator adapted to simultaneously, conveniently and effectively brush and irrigate between teeth and in the gum line.

It is yet another object of the present invention to provide such an oral irrigator having a brush assembly that has a plurality of brushing members disposed in a pattern that facilitates the cleaning process.

It is further object of the present invention to provide such an oral irrigator having a brush assembly adapted to be detachable and replaceable for the purpose of extending the useful life of the device.

These and other objects and advantages of the present invention are achieved by an oral irrigator adapted to work in conjunction with a mechanism for providing pressurized liquid (e.g. a pump) and having a main body with an elongated shaft, a connector, and a receiving cavity for receiving a brush assembly.

DETAILED DESCRIPTION OF THE INVENTION

Figure 1:
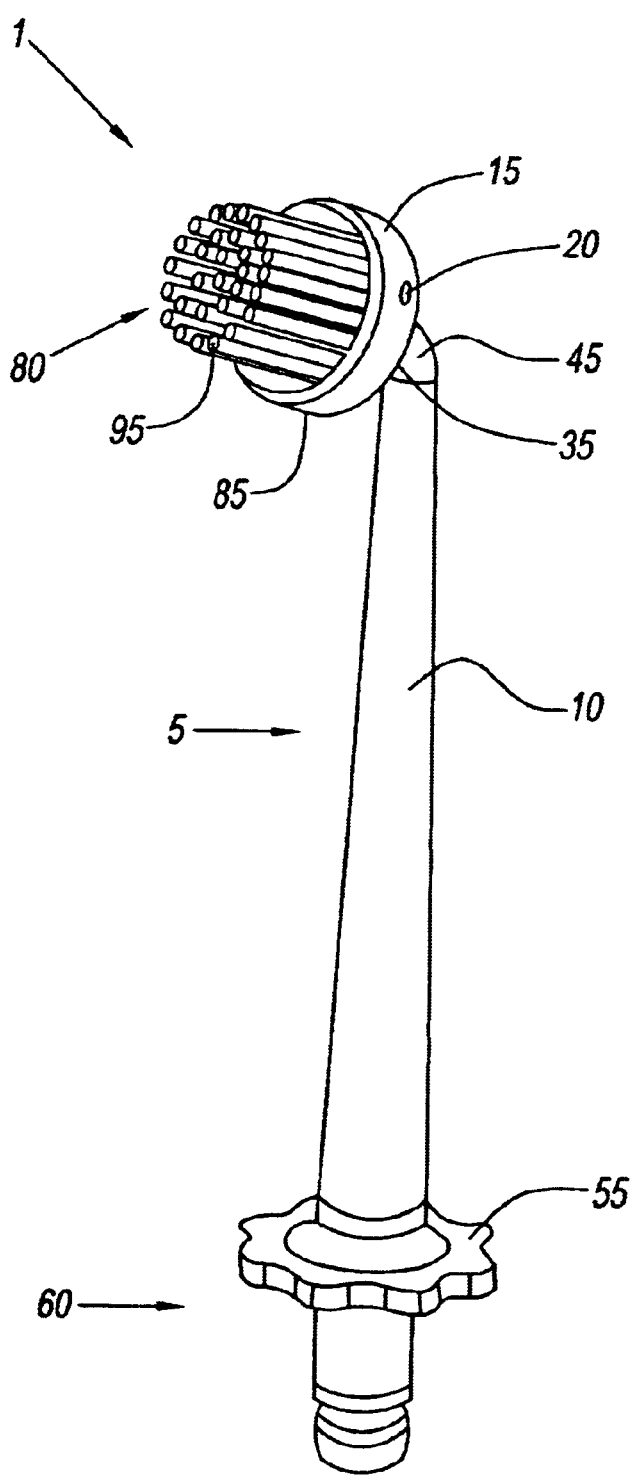
FIG. 1 is a perspective view of an oral irrigator in accordance with a preferred embodiment of the present invention.

Referring to the drawings and in particular, FIG. 1, there is shown an oral irrigator in accordance with a preferred embodiment of the present invention generally represented by reference numeral 1. The oral irrigator 1 has a main body 5. Preferably, main body 5 has an shaft 10 having a neck 45 positioned at one end thereof and a connector 60 positioned at the other end thereof. Main body 5 also preferably includes a receiving cavity 15 connected to neck 45. Connector 60 is adapted to connect oral irrigator 1 to a mechanism for providing pressurized fluid.

Figure 2:
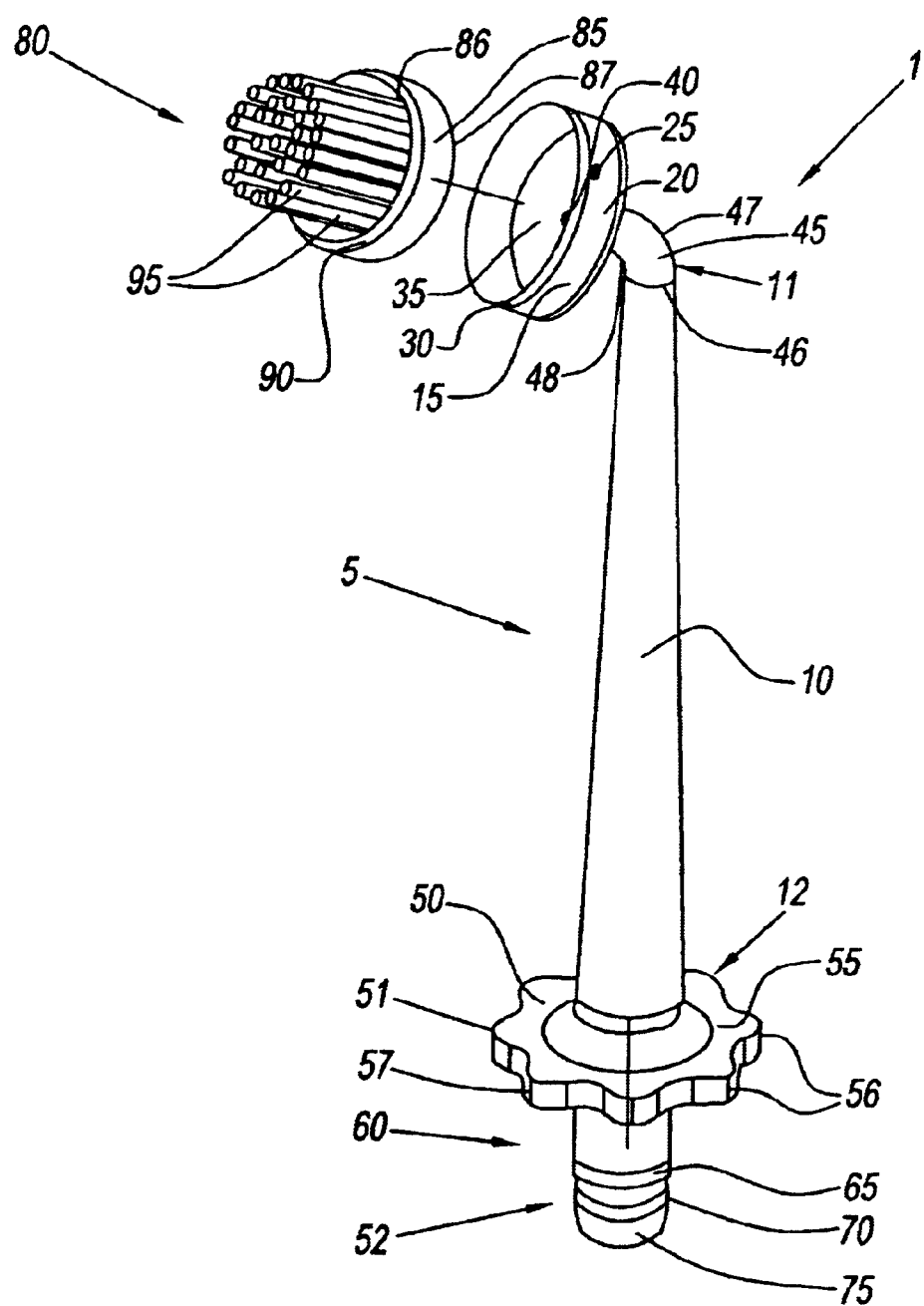
FIG. 2 is an exploded perspective view of the oral irrigator of FIG. 1.

Referring to FIG. 2, shaft 10 has a distal end 12 and a proximal end 11. Preferably, shaft 10 is tapered, with distal end 12 having a greater cross-sectional area than proximal end 11. Shaft 10 may be adjustable having different lengths to provide greater flexibility in reaching different parts of a user's mouth or oral cavity.

Neck 45 preferably is also tapered. It also has a distal end 46 and a proximal end 47. Distal end 46 preferably has a greater cross-sectional area than proximal end 47. The cross-sectional area of distal end 46 corresponds to the cross-sectional area of proximal end 11 of shaft 10. Proximal end 47 of neck 45 is preferably connected to receiving cavity 15. Neck 45 also preferably has a bend 48 therein. Bend 48 is preferably sufficient to improve comfort in use and optimize the cleaning effectiveness of oral irrigator 1.

Receiving cavity 15 preferably has a side wall 20 and a bottom surface 35 to form a cup-like structure. Receiving cavity 15 preferably has a rounded shape and is preferably adapted to receive brush assembly 80 with base structure 85. Within the scope of this invention, receiving cavity 15 and brush assembly 80 can also take many different forms and be arranged in different configurations. For example, brush assembly 80 can, by methods known in the art, be made rotatably driven.

In another embodiment, receiving cavity 15 preferably has a distended rim 30 on the inner surface of side wall 20. Distended rim 30 is preferably adapted to engage a groove 90 on base structure 85 of brush assembly 80. Side wall 20 preferably also has a small aperture 25 therein. Aperture 25 is preferably adapted to receive a device (not shown) that functions to allow a user to dislodge distended rim 30 from groove 90. This allows a user to remove and replace brush assembly 80.

In still another embodiment, base structure 85 has a second side surface 87 preferably permanently sealed within receiving cavity 15 by ultrasonic welding, such that first side 86 of base structure 85 is essentially flush with side wall 20. Other modifications are also foreseeable and in the scope of the present invention.

In any embodiment, structure 85 preferably has a circular disk shape and a plurality of bristle tufts 95 extending from a first side 86 thereof. Connector 60 preferably has a transition section 50 that provides a smooth or gradual transition from distal end 12 of shaft 10 to an outwardly flared flange 55. Flange 55 preferably has a side wall with a plurality of crests 56 and troughs 57 that function to improve gripping and handling of oral irrigator 1. Preferably, flange 55 separates transition section 50 from an engaging section 65 of connector 60. Engaging section 65 preferably has an undercut 70 therein with a tapered inserter 75 adjacent thereto in order to facilitate connection to take pressurized fluid.

Figure 3:
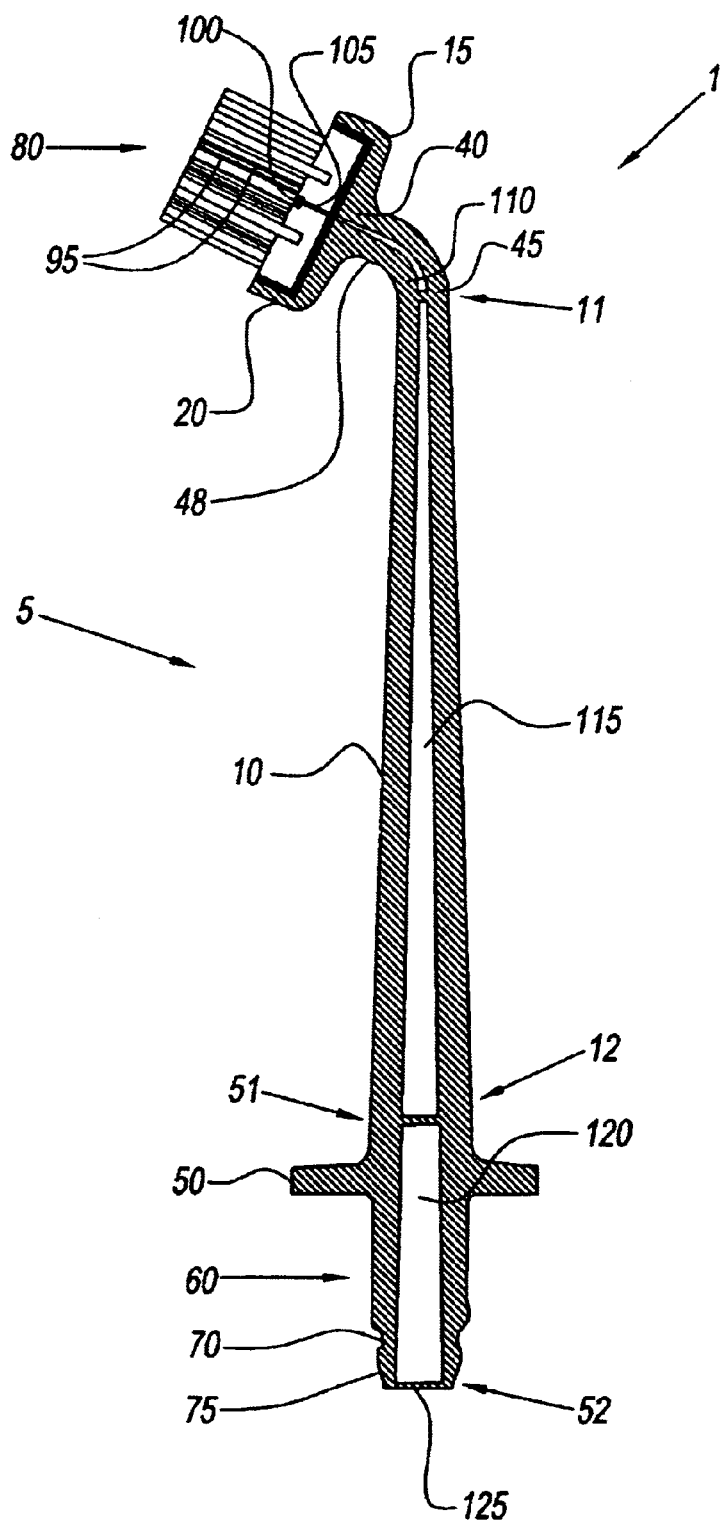
FIG. 3 is a side, section view of the oral irrigator of FIG. 1.

Referring to FIGS. 2 and 3, preferably at least one outlet orifice 40, shown clearly in FIG. 2, is centrally disposed in bottom surface 35 of receiving cavity 15. Outlet orifice 40 is preferably in fluid communication with a base fluid channel 105. Base fluid channel 105 is centrally located in base structure 85. Base fluid channel 105 preferably has a fluid outlet 100 adapted to discharge a pressurized fluid stream. Base fluid channel 105 preferably has a uniform cross-sectional area throughout.

Outlet orifice 40 and base fluid channel 105 are in fluid communication with a main body fluid channel 107. Main body fluid channel 107 preferably passes through shaft 10 and connector 60. Main body fluid channel 107 also can preferably be divided into at least a neck fluid channel 110, a shaft fluid channel 115 and a connector fluid channel 120.

Neck fluid channel 110 is preferably tapered such that it has a cross-sectional area at distal end 46 that is larger than the cross-sectional area at proximal end 47. Neck channel 110 is also preferably in fluid communication with shaft fluid channel 115.

Shaft fluid channel 115 is preferably centrally located in shaft 10 and tapered such that it has a cross-sectional area at distal end 12 that is larger than the cross-sectional area at proximal end 11. The cross-sectional area of shaft fluid channel 115 at proximal end 11 is preferably the same as the cross-sectional area of neck channel 110 at distal end 46. Shaft fluid channel 115 preferably is in fluid communication with connector fluid channel 120.

Connector fluid channel 120 has a distal end 52 and a proximal end 51. Connector fluid channel 120 is preferably centrally located in connector 60 and tapered such that cross-sectional area at distal end 52 that is larger than the cross-sectional area at proximal end 51. The cross-sectional area of connector fluid channel 120 at proximal end 51 is preferably the same as the cross-sectional area of shaft fluid channel 115 at distal end 12.

Main body fluid channel 107 can also take many different forms and be arranged in different configurations. For example, each fluid channel 110, 115 and 120 can be adapted with various internal hydraulic steps to alter the pressure and flow of the fluid stream exiting fluid outlet 100. Another example of a possible configuration would be to alter the size and shape of each channel thereby altering the fluid flow.

Figure 4:
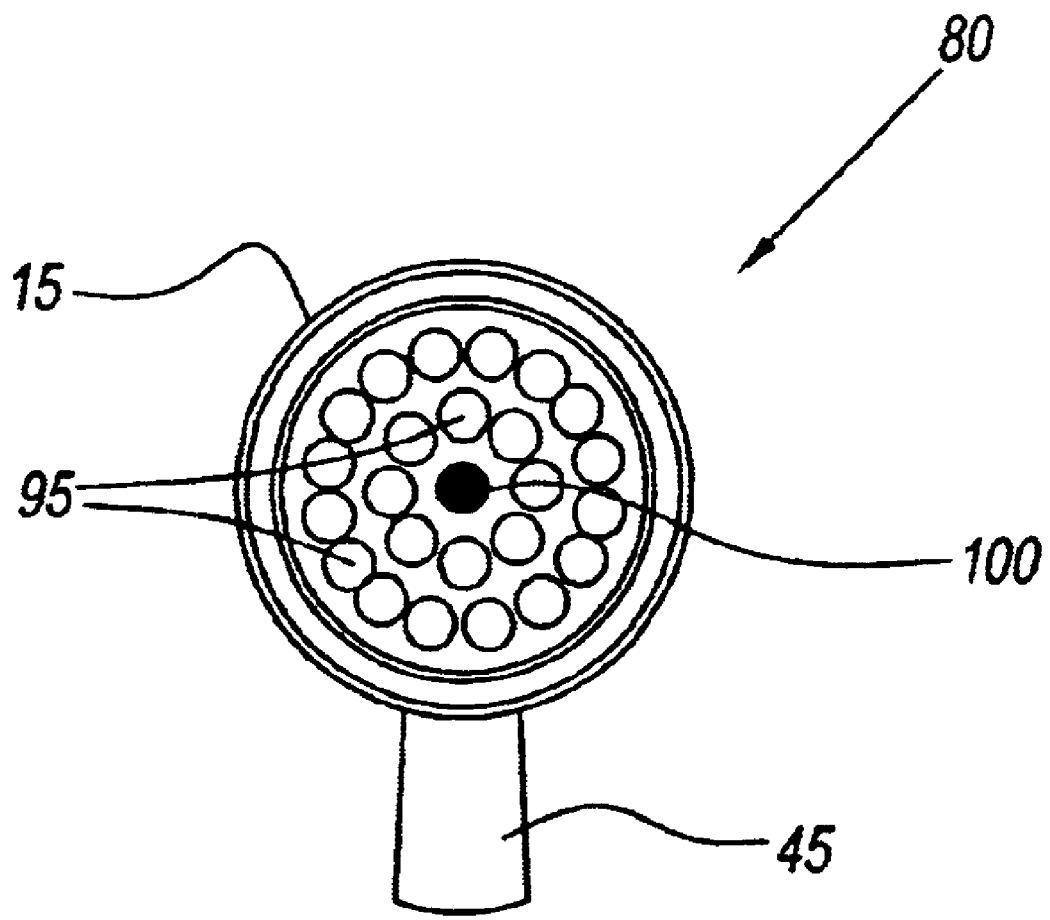
FIG. 4 is a plan view of the oral irrigator of FIG. 1.

Referring to FIG. 4, receiving cavity 15 receives structure 85. Structure 85 preferably has two or more bristle tufts 95 preferably fixed thereto using any suitable method known in the art. The bristle tufts 95 are preferably arranged in two or more circular rows. The bristle tufts 95 preferably have different rigidities. The bristle tufts 95 are of at least one length, but may have two or more different lengths for different cleaning effects. Also, bristle tufts 95 may be configured in a multitude of different patterns. Each pattern providing a different cleaning effect.

Main body fluid channel 107 provides virtually or in fact maximized fluid pressure preferably in at least one fluid stream (not shown). Preferably the at least one fluid stream has a massaging and stimulating effect on the gums. Moreover, brush assembly 80 provides virtually or in fact maximized brush cleaning effect preferably with bristle tufts 95 arranged in a plurality of circular rows to improve the actual surface contact on and between the teeth. Still further, the configuration of bristle tufts 95 and main body 60 with main body fluid channel 107 is such so as to preferably provide for the virtual or in fact maximized cleaning effect that can result from the combination of both irrigation and brushing. Thus, the present invention is preferably configured to massage and stimulate the gums and more particularly, to simultaneously, conveniently and effectively brush and irrigate between teeth and in the gum line.

The present invention having been thus described with particular reference to the preferred forms thereof, it will be obvious that various changes and modifications may be made therein without departing from the spirit of the present invention as defined herein.

What is claimed is:

1. An oral irrigator comprising:
   a main body having an elongated shaft with a first end and a second end, a connector being connected to said first end of said elongated shaft, and a neck being connected to said second end of said elongated shaft,
   a receiving cavity having a side wall and a bottom surface forming a cup-like shape, said bottom surface having at least one outlet orifice centrally disposed therein;
   a brush assembly having a base with a plurality of bristle tufts disposed thereon, said base having at least one centrally disposed aperture therein, said base fitting in said receiving cavity, said at least one aperture being in fluid communication with said at least one outlet orifice; and
   a tapered fluid channel in said main body, said fluid channel being in fluid communication with said at least one outlet orifice.

2. The irrigator of claim 1, wherein said elongated shaft is tapered with said second end having a smaller cross-sectional area than said first end.

3. The irrigator of claim 1, wherein said neck is tapered with a proximal end having a smaller cross-sectional area than a distal end.

4. The irrigator of claim 1, wherein said neck is angled with respect to said elongated shaft.

5. The irrigator of claim 1, wherein said connector has a flange and an engaging section, said engaging section having an undercut adjacent to a tapered inserter.

6. The irrigator of claim 1, wherein said cup-like shape is circular.

7. The irrigator of claim 6, wherein said base is a circular disk for being placed in said receiving cavity.

8. The irrigator of claim 1, wherein said base is removable, and wherein said plurality of bristle tufts form a plurality of circular rows.

9. The irrigator of claim 1, wherein said plurality of bristle tufts have different rigidities.

10. The irrigator of claim 1, wherein said plurality of bristle tufts have more than one length.

11. An oral irrigator comprising:
    a main body having an elongated shaft with a first end and a second end, a connector being connected to said first end of said elongated shaft, and a neck being connected to said second end of said elongated shaft, said neck being connected to a receiving cavity; and
    a brush assembly having a disk shaped base with a plurality of bristle tufts disposed in a plurality of circular rows on said base, said base having at least one aperture centrally disposed therein, said base fitting in said receiving cavity,
    wherein said plurality of bristle tufts have different rigidities and are of more than one length.

12. The irrigator of claim 11, further comprising a main body fluid channel disposed in said main body and in fluid communication with said at least one centrally disposed aperture of said brush assembly.

13. The irrigator of claim 11, wherein said elongated shaft and said neck are tapered.

14. The irrigator of claim 11, wherein said connector has an engaging section, an undercut, and a tapered inserter.

* * * * *